United States Patent
Schmitt

(12) 
(10) Patent No.: US 6,591,122 B2
(45) Date of Patent: Jul. 8, 2003

(54) DEVICE AND METHOD FOR MONITORING BODY FLUID AND ELECTROLYTE DISORDERS

(75) Inventor: Joseph M. Schmitt, Andover, MA (US)

(73) Assignee: Nellcor Puritan Bennett Incorporated, Pleasanton, CA (US)

(*) Notice: Subject to any disclaimer, the term of this patent is extended or adjusted under 35 U.S.C. 154(b) by 51 days.

(21) Appl. No.: 09/810,918

(22) Filed: Mar. 16, 2001

(65) Prior Publication Data

US 2002/0161287 A1 Oct. 31, 2002

(51) Int. Cl.$^7$ .................................................. A61B 5/00
(52) U.S. Cl. ........................................................ 600/310
(58) Field of Search .............................. 600/310, 306, 600/307, 476, 407, 551; 356/320

(56) References Cited

U.S. PATENT DOCUMENTS

| | | | |
|---|---|---|---|
| 4,066,068 A | | 1/1978 | Nilsson et al. |
| 4,364,008 A | | 12/1982 | Jacques |
| 4,711,244 A | | 12/1987 | Kuzara |

(List continued on next page.)

FOREIGN PATENT DOCUMENTS

| | | | |
|---|---|---|---|
| FR | 2710517 | * | 4/1995 |
| JP | 4-40940 | * | 2/1992 |
| JP | 5-329163 | * | 12/1993 |
| JP | 11-244266 | * | 9/1999 |
| WO | 98/34097 | * | 8/1998 |
| WO | 00/71025 | * | 11/2000 |

OTHER PUBLICATIONS

Lucassen, G., et al., "Water Content and Water Profiles in Skin Measured by FTIR and Raman Spectroscopy," Proc. SPIE, vol. 4162, pp 39–45 (2000).*

Martin, Kathleen, "In Vivo Measurements of Water in Skin by Near–Infrared Reflectance," Applied Spectroscopy, vol. 52, No. 7, 1998, pp 1001–7.*

Takeo, T. et al., "Skin Hydration State Estimation Using a Fiber–Optic Refractometer," Applied Optics, vol. 33. No. 19, Jul. 1994, p. 4267–72.*

(List continued on next page.)

Primary Examiner—John A. Jeffery
(74) Attorney, Agent, or Firm—Townsend & Townsend & Crew LLP

(57) ABSTRACT

A device and a method for measuring body fluid-related metrics using spectrophotometry to facilitate therapeutic interventions aimed at restoring body fluid balance. The specific body fluid-related metrics include the absolute volume fraction of water in the extravascular and intravascular tissue compartments, as well as the shifts of water between these two compartments. The absolute volume fraction of water is determined using algorithms where received radiation measured at two or more wavelengths are combined to form either a single ratio, a sum of ratios or ratio of ratios of the form $\log[R(\lambda_1)/R(\lambda_2)]$ in which the received radiation in the numerator depends primarily on the absorbance of water and the received radiation in the denominator depends primarily on the absorbance of water and the sum of the absorbances of non-heme proteins, lipids and water in tissue. The difference between the fraction of water in the intravascular fluid volume ("IFV") and extravascular fluid volume ("EFV") compartments are also determined using a differential method that takes advantage of the observation that pulsations caused by expansion of blood vessels in the skin as the heart beats produce changes in the received radiation at a particular wavelength that are proportional to the difference between the effective absorption of light in the blood and the surrounding tissue. This difference, integrated over time, provides a measure of the quantity of the fluid that shifts into and out of the capillaries. A mechanism for mechanically inducing a pulse is built into the device to improve the reliability of measurements of IFV-EFV under weak-pulse conditions.

38 Claims, 4 Drawing Sheets

U.S. PATENT DOCUMENTS

| | | | |
|---|---|---|---|
| 4,723,554 A | | 2/1988 | Oman et al. |
| 4,805,623 A | | 2/1989 | Jobsis |
| 4,850,365 A | | 7/1989 | Rosenthal |
| 4,860,753 A | | 8/1989 | Amerena |
| 5,086,781 A | | 2/1992 | Bookspan |
| 5,146,091 A | | 9/1992 | Knudson |
| 5,277,181 A | | 1/1994 | Mendelson et al. |
| 5,337,745 A | | 8/1994 | Benaron |
| 5,348,004 A | | 9/1994 | Hollub |
| 5,377,674 A | | 1/1995 | Kuestner |
| 5,499,627 A | | 3/1996 | Steuer et al. |
| 5,615,689 A | | 4/1997 | Kotler |
| 5,701,902 A | * | 12/1997 | Vari et al. .......... 600/476 |
| 5,720,284 A | | 2/1998 | Aoyagi et al. |
| 5,747,789 A | | 5/1998 | Godik |
| 5,755,672 A | * | 5/1998 | Arai et al. .......... 600/547 |
| 5,788,643 A | | 8/1998 | Feldman |
| 5,853,364 A | | 12/1998 | Baker, Jr. et al. |
| 5,906,582 A | * | 5/1999 | Kondo et al. .......... 600/500 |
| 6,149,591 A | * | 11/2000 | Henderson et al. .......... 600/407 |
| 6,336,044 B1 | * | 1/2002 | Ghiassi et al. .......... 600/476 |
| 6,370,426 B1 | * | 4/2002 | Campbell et al. .......... 600/547 |
| 6,442,408 B1 | * | 8/2002 | Wenzel et al. .......... 600/310 |

OTHER PUBLICATIONS

Attas, M. et al., "Long–Wavelength Near–Infrared Spectroscopic Imaging for In–Vivo Skin Hydration Measurements," Vibrational Spectroscopy (Feb. 28, 2002), vol. 28,, No. 1, p. 37–43.*

Edwardson, P. et al, "The Use of FT–IR for the Determination of Stratum Corneum Hydration In Vitro and In Vivo," J. Pharmaceutical & Biomed. Analysis, vol. 9, Nos. 10–12, pp. 1089–1094, 1991.*

Johnson et al., "Monitoring of Extracellular and Total Body Water during Hemodialysis Using Multifrequency BioElectrical Impedance Analysis," Kidney and Blood Pressure Research, 19:94–99 (1996).

Thompson et al., Can bioelectrical impedance be used to measure total body water in dialysis patients? Physiol. Meas., 14:455–461 (1993).

* cited by examiner

“DEVICE AND METHOD FOR MONITORING BODY FLUID AND ELECTROLYTE DISORDERS

BACKGROUND OF THE INVENTION

The maintenance of body fluid balance is of foremost concern in the care and treatment of critically ill patients, yet physicians have access to few diagnostic tools to assist them in this vital task. Patients with congestive heart failure, for example, frequently suffer from chronic systemic edema, which must be controlled within tight limits to ensure adequate tissue perfusion and prevent dangerous electrolyte disturbances. Dehydration of infants and children suffering from diarrhea can be life-threatening if not recognized and treated promptly.

The most common method for judging the severity of edema or dehydration is based on the interpretation of subjective clinical signs (e.g., swelling of limbs, dry mucous membranes), with additional information provided by measurements of the frequency of urination, heart rate, serum urea nitrogen SUN/creatinine ratios, and blood electrolyte levels. None of these variables alone, however, is a direct and quantitative measure of water retention or loss.

The indicator-dilution technique, which provides the most accurate direct measure of water in body tissues, is the present de facto standard for assessment of body fluid distribution. It is, however, an invasive technique that requires blood sampling. Additionally, a number of patents have disclosed designs of electrical impedance monitors for measurement of total body water. The electrical-impedance technique is based on measuring changes in the high-frequency (typically 10 KHz–1 MHz) electrical impedance of a portion of the body. Mixed results have been obtained with the electrical-impedance technique in clinical studies of body fluid disturbances as reported by various investigators. The rather poor accuracy of the technique seen in many studies point to unresolved deficiencies of these designs when applied in a clinical setting.

Therefore, there exists a need for methods and devices for monitoring total body water fractions which do not suffer from problems due to their being invasive, subjective and inaccurate.

SUMMARY OF THE INVENTION

Embodiments of the present invention provide devices and methods that measure body fluid-related metrics using spectrophotometry to facilitate therapeutic interventions aimed at restoring body fluid balance. The specific body fluid-related metrics include the absolute volume fraction of water in the extravascular and intravascular tissue compartments, as well as the shifts of water between these two compartments. The absolute volume fraction of water is determined using algorithms where received radiation measured at two or more wavelengths are combined to form either a single ratio, a sum of ratios or ratio of ratios of the form log $[R(\lambda_1)/R(\lambda_2)]$ in which the received radiation in the numerator depends primarily on the absorbance of water and the received radiation in the denominator depends primarily on the absorbance of water and the sum of the absorbances of non-heme proteins and lipids in tissue.

The difference between the fraction of water in the intravascular fluid volume ("IFV") and extravascular fluid volume ("EFV") compartments are also determined using a differential method that takes advantage of the observation that pulsations caused by expansion of blood vessels in the skin, as the heart beats, produce changes in the received radiation at a particular wavelength that are proportional to the difference between the effective absorption of light in the blood and the surrounding tissue. This difference, integrated over time, provides a measure of the quantity of the fluid that shifts into and out of the capillaries. A mechanism for mechanically inducing a pulse is built into the device to improve the reliability of measurements of IFV-EFV under weak-pulse conditions.

For a fuller understanding of the nature and advantages of the embodiments of the present invention, reference should be made to the following detailed description taken in conjunction with the accompanying drawings.

DESCRIPTION OF THE SPECIFIC EMBODIMENTS

Figure 1:
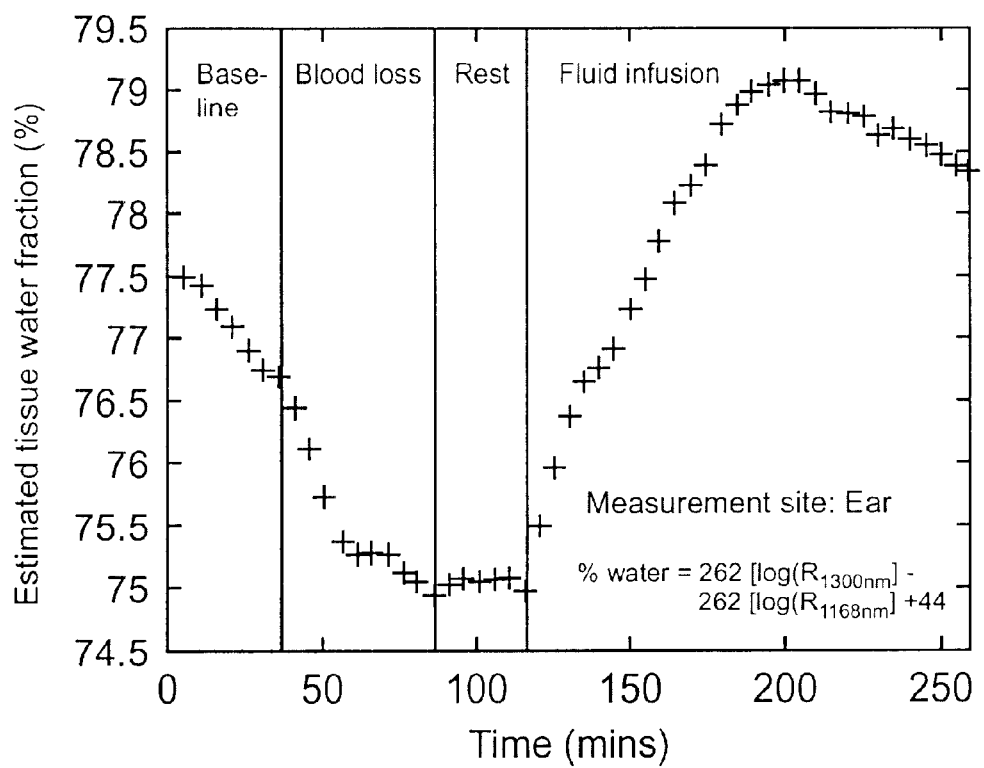
FIG. 1 is a graph showing tissue water fraction measured on the ear of a pig during an experiment using reflectance measurements at two wavelengths.

Embodiments of the present invention overcome the problems of invasiveness, subjectivity, and inaccuracy from which previous methods for body fluid assessment have suffered. The method of diffuse reflectance near-infrared ("NIR") spectroscopy is employed to measure the absolute fraction of water in skin. An increase or decrease in the free (non protein-bound) water content of the skin produces unique alterations of its NIR reflectance spectrum in three primary bands of wavelengths (1100–1350 nm, 1500–1800 nm, and 2000–2300 nm) in which none-heme proteins (primarily collagen and elastin), lipids, and water absorb. According to the results of numerical simulations and experimental studies carried out by the inventor, the tissue water fraction $f_w$, defined spectroscopically as the ratio of the absorbance of water and the sum of the absorbances of none-heme proteins, lipids, and water in the tissue, can be measured accurately in the presence of nonspecific scattering variation, temperature, and other interfering variables.

In embodiments of this invention, the apparatus and its associated measurement algorithm are designed according to the following guidelines:

1. To avoid the shunting of light through the superficial layers of the epidermis, the light source and detector in optical reflectance probe have low numerical apertures, typically less than 0.3.
2. The spacing between the source and detector in the probe is in the range of 1–5 mm to confine the light primarily to the dermis.
3. The reflectances are measured at wavelengths greater than 1150 nm to reduce the influence of hemoglobin absorption.

4. To ensure that the expression that relates the measured reflectances and $f_w$ yields estimates of water fraction that are insensitive to scattering variations, the lengths of the optical paths through the dermis at the wavelengths at which the reflectances are measured are matched as closely as possible. This matching is achieved by judicious selection of wavelength sets that have similar water absorption characteristics. Such wavelength sets may be selected from any one of the three primary wavelength bands (1100–1350 nm, 1500–1800 nm, and 2000–2300 nm) discussed above. Wavelength pairs or sets are chosen from within one of these three primary bands, and not from across the bands. More particularly the wavelength pair of 1180 and 1300 nm are one such wavelength set where the lengths of the optical paths through the dermis at these wavelengths are matched as closely as possible.

5. To ensure that the expression that relates the measured reflectances and $f_w$ yields estimates of water fraction that are insensitive to temperature variations, the wavelengths at which the reflectances are measured are chosen to be either close to temperature isosbestic wavelengths in the water absorption spectrum or the reflectances are combined in a way that cancels the temperature dependencies of the individual reflectances. Typically, absorption peaks of various biological tissue components may shift with variations in temperature. Here, wavelengths are selected at points in the absorption spectrum where no significant temperature shift occurs. Alternately, by knowing the value of this temperature shift, wavelength sets may be chosen such that any temperature shift is mathematically canceled out when optical measurements are combined to compute the value of a tissue water metric. Such wavelength sets may be selected from any one of the three primary wavelength bands (1100–1350 nm, 1500–1800 nm, and 2000–2300 nm) discussed above. Wavelength pairs or sets are chosen from within one of these three primary bands, and not from across the bands. More particularly the wavelength pair of 1180 and 1300 nm are one such pair of temperature isosbestic wavelengths in the water absorption spectrum.

6. The reflectances measured at two or more wavelengths are combined to form either a single ratio, a sum of ratios or ratio of ratios of the form $\log[R(\lambda_1)/R(\lambda_2)]$ in which the reflectance in the numerator depends primarily on the absorbance of water and the reflectance in the denominator is nearly independent of the fraction of solids (lipids and proteins) in the tissue.

Thus, in one embodiment of the present invention the water fraction, $f_w$, is estimated according to the following equation, based on the measurement of reflectances, $R(\lambda)$ at two wavelengths and the empirically chosen calibration constants $c_0$ and $c_1$:

$$f_w = c_1 \log[R(\lambda_1)/R(\lambda_2)] + c_0 \quad (1)$$

Numerical simulations and in vitro experiments indicate that $f_w$ can be estimated with an accuracy of approximately +/−2% over a range of water contents between 50 and 80% using Equation (1), with reflectances $R(\lambda)$ measured at two wavelengths and the calibration constants $c_0$ and $c_1$ chosen empirically. Examples of suitable wavelength pairs are $\lambda_1=1300$ nm, $\lambda_2=1168$ nm, and $\lambda_1=1230$ nm, $\lambda_2=1168$ nm.

The ability to measure changes in the water content in the ear of a pig using two-wavelength NIR reflectometry was demonstrated experimentally in a study in which a massive hemorrhage was induced in a pig and the lost blood was replaced with lactated Ringer's solution over a period of several hours. Ringer's solution is a well-known solution of salts in boiled and purified water. FIG. 1 shows the water fraction in the skin of the ear of a pig, measured using Equation (1) with $\lambda_1=1300$ nm and $\lambda_2=1168$ nm. Referring to FIG. 1, it should be noted that experimental observations of concern to this embodiment commence when the lactated Ringer's solution was infused 120 minutes after the start of the experiment. It should also be noted that the drift in the water fraction from approximately 77.5% to 75% before the infusion is not related to this infusion experiment, but is related to the base-line hemorrhage portion of the experiment. The results show that the method of the present embodiment correctly reflects the effect of the infusion by showing an increase in tissue water fraction from approximately 75% to 79% while the infusion is continuing. These data suggest that the disclosed embodiment has a clear value as a monitor of rehydration therapy in a critical care setting.

In another embodiment of the present invention the water fraction, $f_w$, is estimated according to Equation (2) below, based on the measurement of reflectances, $R(\lambda)$ at three wavelengths and the empirically chosen calibration constants $c_0$, $c_1$ and $c_2$:

$$f_w = c_2 \log[R(\lambda_1)/R(\lambda_2)] + c_1 \log[R(\lambda_2)/R(\lambda_3)] + c_0 \quad (2)$$

Better absolute accuracy can be attained using Equation (2) which incorporates reflectance measurements at an additional wavelength. The results of in vitro experiments on excised skin indicate that the wavelength triple ($\lambda_1=1190$ nm, $\lambda_2=1170$ nm, $\lambda_3=1274$ nm) yields accurate estimates of skin water content based on Equation (2).

In yet another embodiment of the present invention the water fraction, $f_w$, is estimated according to Equation (3) below, based on the measurement of reflectances, $R(\lambda)$ at three wavelengths and the empirically chosen calibration constants $c_0$ and $c_1$:

$$f_w = c_1 \frac{\log[R(\lambda_1)/R(\lambda_2)]}{\log[R(\lambda_3)/R(\lambda_2)]} + c_0 \quad (3)$$

Figure 2:
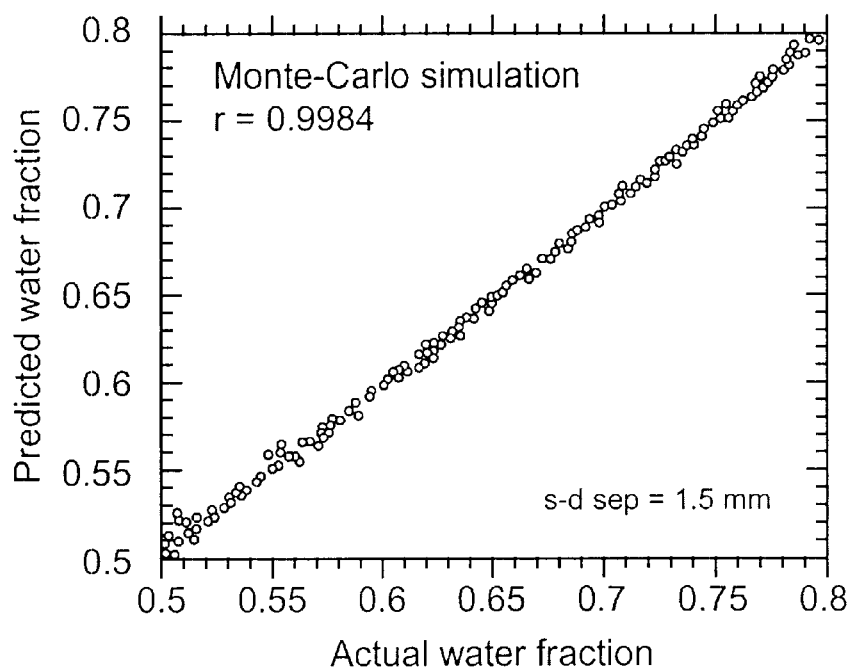
FIG. 2 is a graph showing an example regression for prediction of water from reflectances measured at three wavelengths.

Better absolute accuracy can be attained using Equations (3), as is attained using Equations (2), which also incorporates reflectance measurements at an additional wavelength. Numerical simulations as shown in FIG. 2 indicate that an accuracy better than +/−0.5% can be achieved using Equation (3), with reflectances measured at three closely spaced wavelengths: $\lambda_1=1710$ nm, $\lambda_2=1730$ nm, and $\lambda_3=1740$ nm.

Individuals skilled in the art of near-infrared spectroscopy would recognize that, provided that the aforementioned guidelines are followed, additional terms can be added to Equations (1)–(3) to incorporate reflectance measurements made at more than three wavelengths and thus improve accuracy further.

Figure 3:
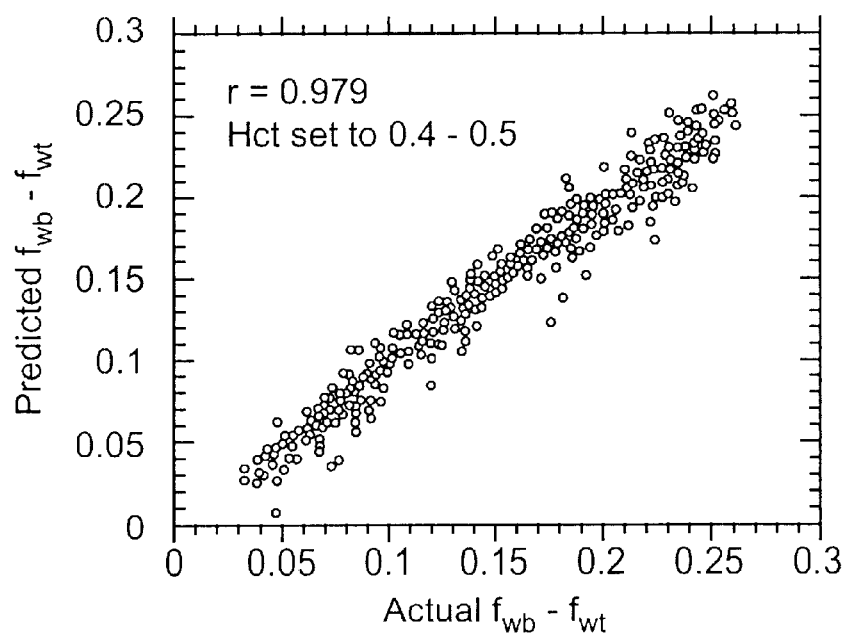
FIG. 3 is a graph showing an example regression of a two-wavelength algorithm for determination of the difference between the intravascular and extravascular water fraction from pulsatile reflectances measured two wavelengths.

An additional embodiment of the disclosed invention provides the ability to quantify shifts of fluid into and out of the bloodstream through a novel application of pulse spectrophotometry. This additional embodiment takes advantage of the observation that pulsations caused by expansion of blood vessels in the skin as the heart beats produce changes in the reflectance at a particular wavelength that are proportional to the difference between the effective absorption of light in the blood and the surrounding interstitial tissues. Numerical simulation indicate that, if wavelengths are chosen at which water absorption is sufficiently strong, the difference between the fractions of water in the blood, $f_w^{blood}$ and surrounding tissue, $f_w^{tissue}$ is proportional to the ratio of the dc-normalized reflectance changes ($\Delta R/R$) measured at two wavelengths, according to Equation (4) below:

$$f_w^{blood} - f_w^{tissue} = c_1 \left(\frac{\Delta R}{R}\right)_{\lambda_1} / \left(\frac{\Delta R}{R}\right)_{\lambda_2} + c_0, \quad (4)$$

where $c_0$ and $c_1$ are empirically determined calibration constants. This difference, integrated over time, provides a measure of the quantity of fluid that shifts into and out of the capillaries. FIG. 3 shows the prediction accuracy expected for the wavelength pair $\lambda_1$=1320 nm and $\lambda_2$=1160 nm.

Figure 4:
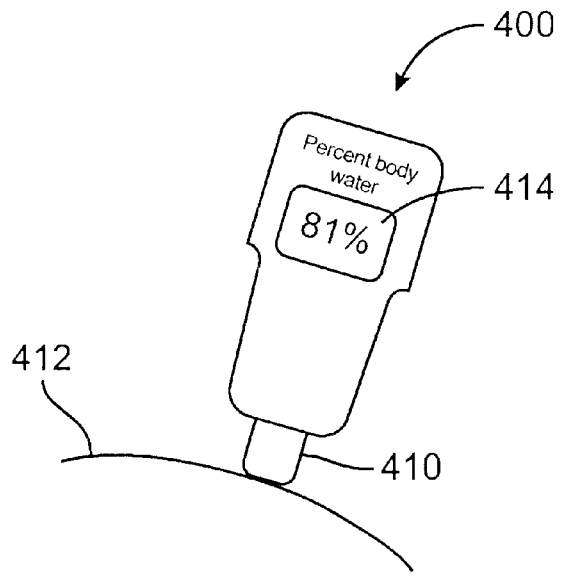
FIG. 4 is a diagram of an intermittent-mode version of a fluid monitor.
Figure 5:
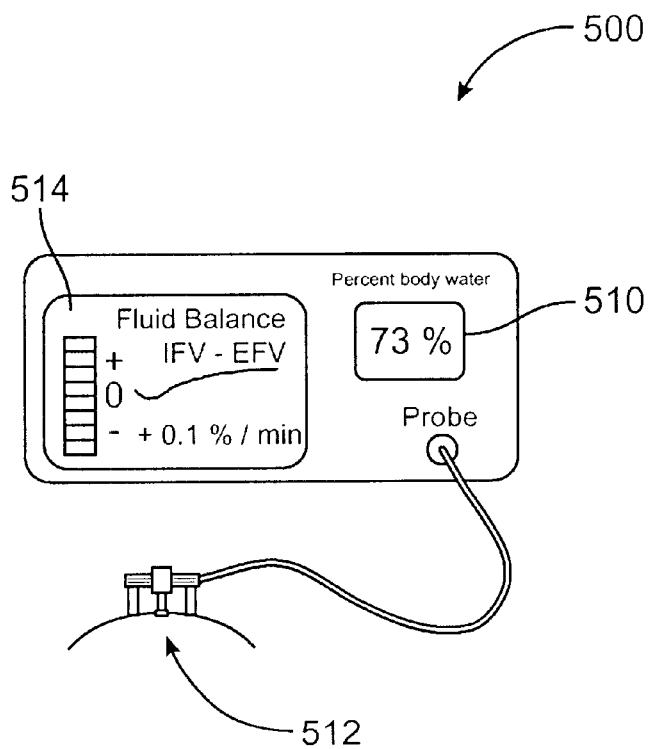
FIG. 5 is a diagram of a continuous-mode version of a fluid monitor.

FIGS. 4 and 5 show diagrams of two different versions of an instrument for measuring the amount of water in body tissues. The simplest version of the instrument 400 shown in FIG. 4 is designed for handheld operation and functions as a spot checker. Pressing the spring-loaded probe head 410 against the skin 412 automatically activates the display of percent tissue water 414. The use of the spring-loaded probe head provides the advantages of automatically activating the display device when needed and turning the device off when not in use, thereby extending device and battery life. Moreover, this unique use of a spring-loaded probe also provides the force needed to improve the reliability of measurements. Percent tissue water represents the absolute percentage of water in the skin beneath the probe (typically in the range 0.6–0.9). The force exerted by a spring or hydraulic mechanism (not shown) inside the probe head 410 pushes out most of the blood in the skin below the probe to reduce the error caused by averaging the intravascular and extravascular fluid fractions. A pressure transducer (not shown) within the probe head 410 measures the compressibility of the skin for deriving an index of the fraction of free (mobile) water.

The more advanced version of the fluid monitor 500 shown in FIG. 5 is designed for use as a critical-care monitor. In addition to providing a continuous display of the absolute volume fraction of water 510 at the site of measurement 512, it also provides a trend display of the time-averaged difference between the intravascular fluid volume ("IFV") and extravascular fluid volume ("EFV") fractions 514, updated every few seconds. This latter feature would give the physician immediate feedback on the net movement of water into or out of the blood and permit rapid evaluation of the effectiveness of diuretic or rehydration therapy. To measure the IFV-EFV difference, the monitor records blood pulses in a manner similar to a pulse oximeter. Therefore, placement of the probe on the finger or other well-perfused area of the body would be required. In cases in which perfusion is too poor to obtain reliable pulse signals, the IFV-EFV display would be blanked, but the extravascular water fraction would continue to be displayed. A mechanism for mechanically inducing the pulse is built into the probe to improve the reliability of the measurement of IFV-EFV under weak-pulse conditions.

Figure 6:
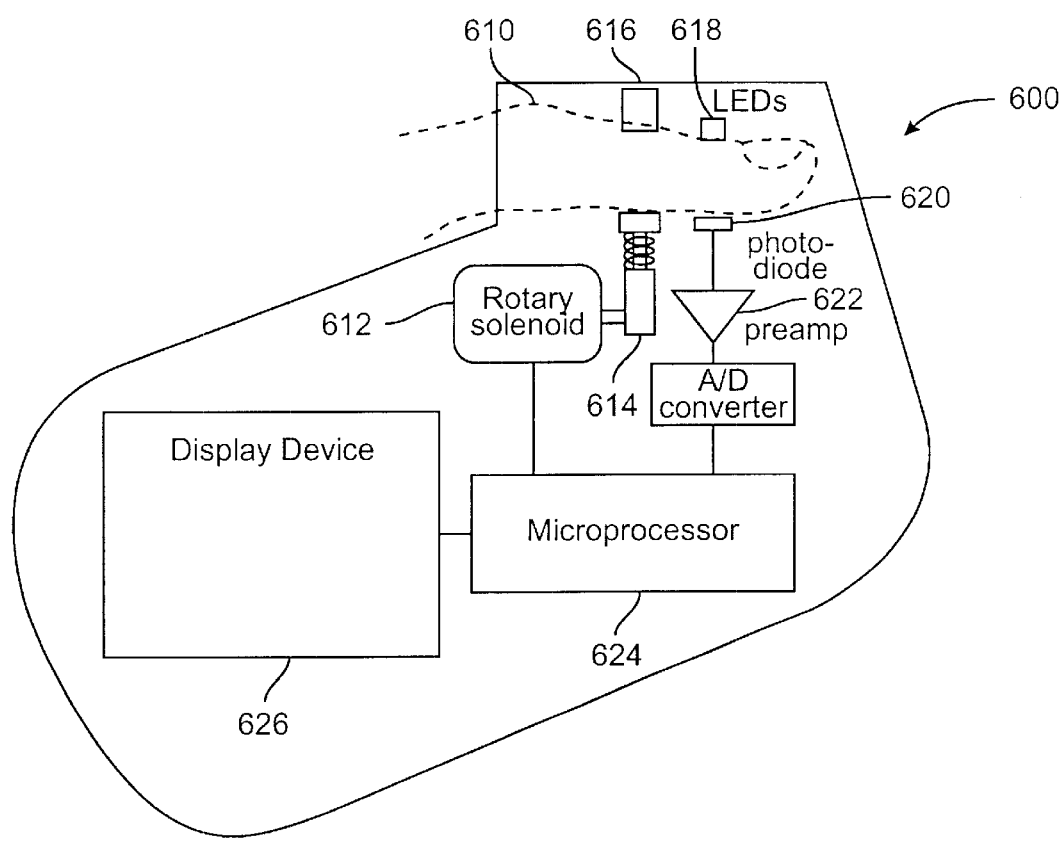
FIG. 6 is a block diagram of a handheld apparatus for noninvasive measurement and display of tissue water.

FIG. 6. is a block diagram of a handheld device 600 for measuring tissue water fraction within the IFV and the EFV, as well as shifts in water between these two compartments with a pulse inducing mechanism. Using this device 600, patient places his/her finger 610 in the probe housing. Rotary solenoid 612 acting through linkage 614 and collar 616 induces a mechanical pulse to improve the reliability of the measurement of IFV-EFV. LEDs 618 emit light at selected wavelengths and photodiode 620 measure the transmitted light. Alternately, the photodiode 620 can be placed adjacent to the LEDs to allow for the measurement of the reflectance of the emitted light. Preamplifier 622 magnifies the detected signal for processing by the microprocessor 624. Microprocessor 624, using algorithms described above, determines the tissue water fraction within the IFV and the EFV, as well as shifts in water between these two compartments, and prepares this information for display on display device 626. Microprocessor 624 is also programmed to handle the appropriate timing between the rotary solenoid's operation and the signal acquisition and processing. The design of the device and the microprocessor integrates the method and apparatus for reducing the effect of noise on measuring physiological parameters as described in U.S. Pat. No. 5,853,364, assigned to Nellcor Puritan Bennett, Inc., now a division of the assignee of the present invention, the entire disclosure of which is hereby incorporated herein by reference. Additionally, the design of the device and the microprocessor also integrates the electronic processor as described in U.S. Pat. No. 5,348,004, assigned to Nellcor Incorporated, now a division of the assignee of the present invention, the entire disclosure of which is hereby incorporated herein by reference.

As will be understood by those skilled in the art, other equivalent or alternative methods for the measurement of tissue water fraction within the IFV and the EFV, as well as shifts in water between these two compartments according to the embodiments of the present invention can be envisioned without departing from the essential characteristics thereof. For example, the device can be operated in either a handheld or a tabletop mode, and it can be operated intermittently or continuously. Moreover, individuals skilled in the art of near-infrared spectroscopy would recognize that additional terms can be added to the algorithms used herein to incorporate reflectance measurements made at more than three wavelengths and thus improve accuracy further. Also, light sources or light emission optics other then LED's including and not limited to incandescent light and narrow-band light sources appropriately tuned to the desired wavelengths and associated light detection optics may be placed within the probe housing which is placed near the tissue location or may be positioned within a remote unit; and which deliver light to and receive light from the probe location via optical fibers. Additionally, although the specification describes embodiments functioning in a backscattering or a reflection mode to make optical measurements of reflectances, other embodiments can be working in a forward-scattering or a transmission mode to make these measurements. These equivalents and alternatives along with obvious changes and modifications are intended to be included within the scope of the present invention. Accordingly, the foregoing disclosure is intended to be illustrative, but not limiting, of the scope of the invention which is set forth in the following claims.

What is claimed is:

1. A device for measuring body fluid-related metrics using optical spectrophotometry comprising:

a probe housing configured to be placed proximal to a tissue location which is being monitored;

light emission optics connected to said housing and configured to direct radiation at said tissue location;

light detection optics connected to said housing and configured to receive radiation from said tissue location; and a processing device configured to process radiation from said light emission optics and said light detection optics to compute said body fluid-related metrics, wherein said body fluid-related metrics comprise absolute volume fractions of water in the extravascular and intravascular bodily tissue compartments and differences between the intravascular fluid volume and extravascular fluid volume fractions.

2. The device of claim 1, further comprising a display device connected to said probe housing and configured to display said body fluid-related metrics.

3. The device of claim 1, wherein said body-fluid metrics are monitored intermittently.

4. The device of claim 1, wherein said body-fluid metrics are monitored continuously.

5. The probe housing of the device of claim 1 further comprising a pressure transducer to measure the compressibility of tissue for deriving an index of a fraction of free water within said tissue.

6. The device of claim 1, wherein said light emission optics are tuned to emit radiation at a plurality of narrow spectral wavelengths chosen so that the biological compound of interest will absorb light at said plurality of narrow spectral wavelengths and so that absorption by interfering species will be at a minimum, where a minimum absorption is an absorption by an interfering species which is less than 10% of the absorption of the biological compound of interest.

7. The device of claim 1, wherein said light emission optics are tuned to emit radiation at a plurality of narrow spectral wavelengths chosen to be preferentially absorbed by tissue water, non-heme proteins and lipids, where preferentially absorbed wavelengths are wavelengths whose absorption is substantially independent of the individual concentrations of non-heme proteins and lipids, and is substantially dependent on the sum of the individual concentrations of non-heme proteins and lipids.

8. The device of claim 1, wherein said light emission optics are tuned to emit radiation at a plurality of narrow spectral wavelengths chosen to ensure that measured received radiation are substantially insensitive to scattering variations and such that the optical path lengths through the dermis at said wavelengths are substantially equal.

9. The device of claim 1, wherein said light emission optics are tuned to emit radiation at a plurality of narrow spectral wavelengths chosen to ensure that measured received radiation from said tissue location are insensitive to temperature variations, where said wavelengths are temperature isosbestic in the water absorption spectrum or said received radiation are combined in a way that substantially cancel temperature dependencies of said individual received radiation when computing tissue water fractions.

10. The device of claim 1, wherein said light emission optics are tuned to emit radiation at a plurality of narrow spectral wavelengths chosen from one of three primary bands of wavelengths of approximately 1100–1350 nm, approximately 1500–1800 nm and approximately 2000–2300 nm.

11. The device of claim 1, wherein said light emission optics and said light detection optics are mounted within said probe housing and positioned with appropriate alignment to enable detection in a transmissive mode.

12. The device of claim 1, wherein said light emission optics and said light detection optics are mounted within said probe housing and positioned with appropriate alignment to enable detection in a reflective mode.

13. The device of claim 1, wherein said light emission optics and said light detection optics are placed within a remote unit and which deliver light to and receive light from said probe housing via optical fibers.

14. The device of claim 1, wherein said light emission optics comprise at least one of a (a) incandescent light source, (b) white light source, and (c) light emitting diode ("LED").

15. The device of claim 1, wherein said processing device receives and compares at least two sets of optical measurements, where the at least first set of optical measurements corresponds to the detection of light whose absorption is primarily due to water, lipids and non-heme proteins, and where the at least second set of optical measurements corresponds to the detection of light whose absorption is primary due to water, and where a comparison of said at least two optical measurements provides a measure of the absolute water fraction within said tissue location.

16. The device of claim 1, wherein said processing device receives and compares at least two sets of optical measurements, where said at least two sets of optical measurements are based on received radiation from at least two wavelengths and which are combined to form either a single ratio of said received radiation, a sum of ratios of said received radiation or ratios of ratios of said received radiation.

17. The device of claim 1, wherein said processing device receives and compares at least two sets of optical measurements from at least two different wavelengths, where absorption of light at said at least two different wavelengths is primarily due to water which is in the vascular blood and in the extravascular tissue, and where a ratio of said at least two measurements provides a measure of a difference between the fractions of water in the blood and surrounding tissue location.

18. The device of claim 1, wherein said body fluid-related metrics comprise tissue water fraction, and where said tissue water fraction, $f_w$ is determined such that $f_w = c_1 \log[R(\lambda_1)/R(\lambda_2)] + c_0$, and where:

calibration constants $c_0$ and $c_1$ are chosen empirically;

$R(\lambda_1)$ is a received radiation at a first wavelength; and $R(\lambda_2)$ is a received radiation at a second wavelength.

19. The tissue water fraction as determined in claim 18, wherein said first and second wavelengths are approximately 1300 nm and approximately 1168 nm respectively.

20. The tissue water fraction as determined in claim 18, wherein said first and second wavelengths are approximately 1230 nm and approximately 1168 nm respectively.

21. The device of claim 1, wherein said body fluid-related metrics comprise tissue water fraction, and where said tissue water fraction, $f_w$ is determined such that $f_w = c_2 \log[R(\lambda_1)/R(\lambda_2)] + c_1 \log[R(\lambda_2)/R(\lambda_3)] + c_0$, and where:

calibration constants $c_0$, $c_1$ and $c_2$ are chosen empirically;

$R(\lambda_1)$ is a received radiation at a first wavelength;

$R(\lambda_2)$ is a received radiation at a second wavelength; and $R(\lambda_3)$ is a received radiation at a third wavelength.

22. The tissue water fraction as determined in claim 21, wherein said first, second and third wavelengths are approximately 1190 nm, approximately 1170 nm and approximately 1274 nm respectively.

23. The device of claim 1, wherein said tissue water fraction, $f_w$ is determined such that $$f_w = c_1 \frac{\log[R(\lambda_1)/R(\lambda_2)]}{\log[R(\lambda_3)/R(\lambda_2)]} + c_0,$$

and where:

calibration constants $c_0$ and $c_1$ are chosen empirically;

$R(\lambda_1)$ is a received radiation at a first wavelength;

$R(\lambda_2)$ is a received radiation at a second wavelength; and $R(\lambda_3)$ is a received radiation at a third wavelength.

24. The tissue water fraction as determined in claim 23, wherein said first, second and third wavelengths are approximately 1710 nm, approximately 1730 nm and approximately 1740 nm respectively.

25. The device of claim 1, wherein said difference between the water fraction in the blood and the water fraction in the extravascular tissue, is determined such that $$f_w^{blood} - f_w^{tissue} = c_1 \left(\frac{\Delta R}{R}\right)_{\lambda_1} / \left(\frac{\Delta R}{R}\right)_{\lambda_2} + c_0,$$

and where:

$f_w^{blood}$ is the water fraction in the blood;
$f_w^{tissue}$ is the water fraction in the extravascular tissue;
calibration constants $c_0$ and $c_1$ are chosen empirically; and $$\left(\frac{\Delta R}{R}\right)_{\lambda_1} / \left(\frac{\Delta R}{R}\right)_{\lambda_2}$$

is the ratio of dc-normalized received radiation changes at a first wavelength, $\lambda_1$ and a second wavelength, $\lambda_2$ respectively, where said received radiation changes are caused by a pulsation caused by expansion of blood vessels in tissue.

26. The body fluid-metric as determined in accordance to claim 25, further comprising an integral of said difference between the water fraction in the blood and the water fraction in the extravascular tissue to provide a measure of the water that shifts into and out of the capillaries.

27. The bodily fluid-metrics as determined in claim 26, wherein said first and second wavelengths are approximately 1320 nm and approximately 1160 nm respectively.

28. A device for measuring body fluid-related metrics using optical spectrophotometry comprising:
    a probe housing configured to be placed proximal to a tissue location which is being monitored;
    light emission optics connected to said housing and configured to direct radiation at said tissue location;
    light detection optics connected to said housing and configured to receive radiation from said tissue location; and
    a processing device configured to process radiation from said light emission optics and said light detection optics to compute said body fluid-related metrics, wherein said probe housing further comprises a spring-loaded probe configured to automatically activate a display device connected to said probe housing when said spring-loaded probe is pressed against a tissue location which is being monitored.

29. A device for measuring body fluid-related metrics using optical spectrophotometry comprising:
    a probe housing configured to be placed proximal to a tissue location which is being monitored;
    light emission optics connected to said housing and configured to direct radiation at said tissue location;
    light detection optics connected to said housing and configured to receive radiation from said tissue location; and
    a processing device configured to process radiation from said light emission optics and said light detection optics to compute said body fluid-related metrics,
    wherein the probe housing further comprises a mechanism for mechanically inducing a pulse within said tissue location to permit measurements of differences between an intravascular fluid volume and an extravascular fluid volume fractions under weak-pulse conditions.

30. A device for measuring body fluid-related metrics using optical spectrophotometry comprising:
    a probe housing configured to be placed proximal to a tissue location which is being monitored;
    light emission optics connected to said housing and configured to direct radiation at said tissue location;
    light detection optics connected to said housing and configured to receive radiation from said tissue location;
    a processing device configured to process radiation from said light emission optics and said light detection optics to compute said body fluid-related metrics; and
    a display device configured to display body fluid-related metrics comprising percent body water and a water balance, where a water balance is the integrated difference between a water fraction in the blood and a water fraction in the extravascular tissue.

31. A device for measuring the absolute volume fraction of water within human tissue using optical spectrophotometry comprising:
    a probe housing configured to be placed proximal to a tissue location which is being monitored;
    light emission optics configured to direct radiation at said tissue location, wherein said light emission optics comprises one of a (a) incandescent light sources, (b) white light sources and (c) light emitting diodes ("LEDs") which are tuned to emit radiation at a plurality of narrow spectral wavelengths chosen to be preferentially absorbed by tissue water, non-heme proteins and lipids;
    a photodiode configured to receive radiation from said tissue location;
    a processing device configured to process radiation from said light emission optics and said light detection optics to compute said absolute volume fraction of water, wherein said processing device receives and compares at least two sets of optical measurements, where the at least first set of optical measurements corresponds to the detection of light whose absorption is primarily due to water, lipids and non-heme proteins, and where the at least second set of optical measurements corresponds to the detection of light whose absorption is primary due to water, and where a comparison of said at least two optical measurements provides a measure of the absolute water fraction within said tissue location;
    a display device connected to said probe housing and configured to display said absolute volume fraction of water; and
    said probe housing further comprising a spring-loaded probe configured to automatically activate said display device when said spring-loaded probe is pressed against a tissue location which is being monitored.

32. A device for measuring a difference between an intravascular fluid volume and an extravascular fluid volume using optical spectrophotometry comprising:
    a probe housing configured to be placed proximal to a tissue location which is being monitored;
    light emission optics configured to direct radiation at said tissue location, wherein said light emission optics comprises one of a (a) incandescent light sources, (b) white light sources or (c) light emitting diodes ("LEDs") which are tuned to emit radiation at a plurality of narrow spectral wavelengths chosen so that the biological compound of interest will absorb light at said plurality of narrow spectral wavelengths and so that absorption by interfering species will be at a minimum;

a photodiode configured to receive radiation from said tissue location;

a processing device configured to process radiation from said light emission optics and said light detection optics to compute said difference between an intravascular fluid volume and an extravascular fluid volume, wherein said processing device receives and compares at least two sets of optical measurements from at least two different wavelengths, where absorption of light at said at least two different wavelengths is primarily due to water which is in the vascular blood and in the extravascular tissue, and where a comparison of said at least two measurements provides a measure of a difference between the fractions of water in the blood and surrounding tissue location; and a display device connected to said probe housing and configured to display said difference between an intravascular fluid volume and an extravascular fluid volume.

33. The device of claim 32, where said difference between an intravascular fluid volume and an extravascular fluid volume is determined such that $$f_w^{blood} - f_w^{tissue} = c_1 \left(\frac{\Delta R}{R}\right)_{\lambda_1} / \left(\frac{\Delta R}{R}\right)_{\lambda_2} + c_0,$$

and where:

$f_w^{blood}$ is the water fraction in the blood;

$f_w^{tissue}$ is the water fraction in the extravascular tissue;

$$\left(\frac{\Delta R}{R}\right)_{\lambda_1} / \left(\frac{\Delta R}{R}\right)_{\lambda_2}$$

is the ratio of dc-normalized received radiation changes at a first wavelength, $\lambda_1$ and a second wavelength, $\lambda_2$ respectively, where said received radiation changes are caused by a pulsation caused by expansion of blood vessels in tissue in response to a heart beat and calibration constants $c_0$ and $c_1$ are chosen empirically.

34. The body fluid-metric as determined in accordance to claim 33 further comprising an integral of said difference between an intravascular fluid volume and an extravascular fluid volume to provide a measure of the water that shifts into and out of the capillaries.

35. The bodily fluid-metrics as determined in claim 33, wherein said first and second wavelengths are 1320 nm and 1160 nm respectively.

36. The device of claim 32 further comprising a mechanism for mechanically inducing a pulse within said tissue location to enhance measurements of said difference between an intravascular fluid volume and an extravascular fluid volume under weak pulse conditions.

37. A method for measuring body fluid-related metrics in a human tissue location using optical spectrophotometry comprising:

placing a probe housing proximal to said tissue location;

emitting radiation at at least two wavelengths using light emission optics configured to direct radiation at said tissue location;

detecting radiation using light detection optics configured to receive radiation from said tissue location;

processing said radiation from said light emission optics and said light detection optics;

computing said body fluid-related metrics, wherein said body fluid-related metrics comprise absolute volume fractions of water in the extravascular and intravascular bodily tissue compartments and differences between the intravascular fluid volume and extravascular fluid volume fraction, where said metrics is determined by:

measuring at least two sets of optical measurements based on received radiation of said at least two wavelengths;

combining said at least two sets of optical measurements to form either a single ratio of said received radiation, a sum of ratios of said received radiation or ratios of ratios of said received radiation to form combinations of received radiation;

determining said metrics from said combinations; and displaying said metrics on a display device connected to said probe housing.

38. A method for measuring a difference between an intravascular fluid volume and an extravascular fluid volume in a human tissue location using optical spectrophotometry comprising:

placing a probe housing proximal to said tissue location;

emitting radiation using light emission optics configured to direct radiation at said tissue location;

detecting radiation using light detection optics configured to receive radiation from said tissue location;

processing said radiation from said light emission optics and said light detection optics;

computing said difference between an intravascular fluid volume and an extravascular fluid volume, and where said difference between an intravascular fluid volume and an extravascular fluid volume is determined such that $$f_w^{blood} - f_w^{tissue} = c_1 \left(\frac{\Delta R}{R}\right)_{\lambda_1} / \left(\frac{\Delta R}{R}\right)_{\lambda_2} + c_0,$$

and where:

$f_w^{blood}$ is the water fraction in the blood;

$f_w^{tissue}$ is the water fraction in the extravascular tissue;

$$\left(\frac{\Delta R}{R}\right)_{\lambda_1} / \left(\frac{\Delta R}{R}\right)_{\lambda_2}$$

is the ratio of dc-normalized received radiation changes at a first wavelength, $\lambda_1$ and a second wavelength, $\lambda_2$ respectively, where said received radiation changes are caused by a pulsation caused by expansion of blood vessels in tissue in response to a heart beat;

calibration constants $c_0$ and $c_1$ are chosen empirically; and displaying said difference between an intravascular fluid volume and an extravascular fluid volume on a display device.

* * * * *